United States Patent
Weiss et al.

(10) Patent No.: US 12,153,105 B2
(45) Date of Patent: Nov. 26, 2024

(54) MONITORING SYSTEM WITH A CAMERA AND NON-METALLIC MIRROR FOR MAGNETIC RESONANCE EXAMINATION SYSTEM

(71) Applicant: KONINKLIJKE PHILIPS N.V., Eindhoven (NL)

(72) Inventors: Steffen Weiss, Hamburg (DE); Jan Hendrik Wuelbern, Hamburg (DE); Christoph Günther Leussler, Hamburg (DE); Julien Thomas Senegas, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 187 days.

(21) Appl. No.: 17/770,679

(22) PCT Filed: Oct. 20, 2020

(86) PCT No.: PCT/EP2020/079415
§ 371 (c)(1),
(2) Date: Apr. 21, 2022

(87) PCT Pub. No.: WO2021/083714
PCT Pub. Date: May 6, 2021

(65) Prior Publication Data
US 2022/0365150 A1 Nov. 17, 2022

(30) Foreign Application Priority Data
Oct. 28, 2019 (EP) ..................... 19205534

(51) Int. Cl.
*G01R 33/28* (2006.01)
*A61B 5/00* (2006.01)
(Continued)

(52) U.S. Cl.
CPC .......... *G01R 33/283* (2013.01); *A61B 5/0077* (2013.01); *A61B 5/055* (2013.01); *G01R 33/56* (2013.01); *G02B 5/09* (2013.01)

(58) Field of Classification Search
CPC .. G01R 33/283; G01R 33/56; G01R 33/5673; G02B 5/0825; G02B 5/09; A61B 5/055; A61B 5/004; A61B 5/0077
See application file for complete search history.

(56) References Cited

U.S. PATENT DOCUMENTS

| | | | |
|---|---|---|---|
| 4,099,838 A | 7/1978 | Cook et al. | |
| 4,650,299 A * | 3/1987 | Stevens | A61B 5/702 359/862 |

(Continued)

FOREIGN PATENT DOCUMENTS

| | | |
|---|---|---|
| EP | 2265979 A | 12/2010 |
| JP | 0928689 A | 2/1997 |

(Continued)

OTHER PUBLICATIONS

Touzet et al., "Multilayer Dielectric Gratings Enable More-Powerful High-Energy Lasers", Sep. 2003 (Year: 2003).*

(Continued)

*Primary Examiner* — Adil Partap S Virk

(57) ABSTRACT

A magnetic resonance examination system with an examination zone (11) and comprising a camera (21) and non-metallic mirror (22), in particular within the examination zone (11), arranging an optical pathway (23) between a portion of the examination zone (11), via the non-metallic mirror (22), and the camera (21). The camera can obtain image information from that portion even if the direct line of sight (28) is blocked. The non-metallic mirror is a dielectric mirror having a macroscopically grated base.

16 Claims, 3 Drawing Sheets

(51) Int. Cl.
*A61B 5/055* (2006.01)
*G01R 33/56* (2006.01)
*G02B 5/09* (2006.01)

(56) References Cited

U.S. PATENT DOCUMENTS

| | | | |
|---|---|---|---|
| 4,923,295 A | | 5/1990 | Sireul et al. |
| 5,825,563 A | | 10/1998 | Anand |
| 6,972,065 B1 | * | 12/2005 | Arnold .............. B32B 17/10018 |
| | | | 156/196 |
| 2002/0163337 A1 | * | 11/2002 | Drobnitzky ............ A61B 5/055 |
| | | | 324/318 |
| 2003/0151809 A1 | * | 8/2003 | Takahashi .............. H04N 13/32 |
| | | | 348/E13.031 |
| 2004/0171927 A1 | | 9/2004 | Lowen et al. |
| 2007/0242806 A1 | * | 10/2007 | Borgmann .............. A61B 6/548 |
| | | | 378/207 |
| 2009/0028292 A1 | * | 1/2009 | Popescu ............... A61B 6/4028 |
| | | | 378/19 |
| 2009/0122278 A1 | * | 5/2009 | Kirschenbaum ... G02B 26/0841 |
| | | | 353/98 |
| 2013/0128611 A1 | * | 5/2013 | Akutsu ................ G03H 1/0248 |
| | | | 359/629 |
| 2015/0065852 A1 | * | 3/2015 | Driemel ................. A61B 5/055 |
| | | | 600/410 |
| 2017/0080298 A1 | | 3/2017 | Yadav |
| 2017/0119320 A1 | * | 5/2017 | Ueda ........................ A61B 5/11 |
| 2017/0123020 A1 | * | 5/2017 | Ohmure ............... G01R 33/283 |
| 2017/0146619 A1 | | 5/2017 | Strauss et al. |
| 2019/0038246 A1 | * | 2/2019 | Hotta ....................... G02B 3/08 |
| 2020/0321908 A1 | | 10/2020 | Anders et al. |
| 2021/0212589 A1 | * | 7/2021 | Zhang .................. A61B 5/0064 |
| 2021/0281819 A1 | * | 9/2021 | Wippermann ........... G02B 5/09 |

FOREIGN PATENT DOCUMENTS

| | | |
|---|---|---|
| JP | 2004041441 A | 2/2004 |
| JP | 2018042892 A | 3/2018 |
| WO | 2005120341 A1 | 12/2005 |
| WO | 2006051497 A1 | 5/2006 |
| WO | 20090112810 A1 | 9/2009 |
| WO | 2019071100 A1 | 4/2019 |

OTHER PUBLICATIONS

Wikipedia https://en.wikipedia.org/wiki/Dielectric_mirror (downloaded Apr. 15, 2022).
De Haan G. and Jeanne V. Robust pulse rate from chrominance-based rPPG. IEE Trans Biomed eng. Oct. 2013; 60(10):2878-86.
Van Gastel M., Stuijk S., de Haan G. Motion robust remote-PPG in infrared. IEE Trans Biomed eng. May 2015; 62(5):1425-33.
International Search Report and Written Opinion from PCT/EP2020/079415 mailed Jan. 21, 2021.

* cited by examiner

MONITORING SYSTEM WITH A CAMERA AND NON-METALLIC MIRROR FOR MAGNETIC RESONANCE EXAMINATION SYSTEM

CROSS REFERENCE TO RELATED APPLICATIONS

This application is a U.S. national phase application of International Application No. PCT/EP2020/079415 filed on Oct. 20, 2020, which claims the benefit of EP application Ser. No. 19/205,534.1 filed on Oct. 28, 2019 and is incorporated herein by reference.

FIELD OF THE INVENTION

The invention pertains to a monitoring system with a camera to monitor the examination region of a magnetic resonance examination system.

BACKGROUND OF THE INVENTION

Such a monitoring system is known from the US-patent application US2017/0146619. The known monitoring system is formed by a camera that is mounted outside the magnetic resonance imaging (MM) device's bore, adjacent to the MRI-device's protective cover. The camera is arranged to image the patient to be examined during operation of the MM-device.

JP H0928689 discloses a mirror installed in the bore of an MRI system and a TV camera for taking an image of a subject mirrored on the mirror. A computer analyzes the image and detects the motion of the subject. The computer determines whether the MR data is to be discarded, taken again or collected, e.g. depending on whether the subject moves out of a limited range. Alternatively, MRI parameters can be optimized to cancel the influence of the motion of the subject.

JP 2018-042892 discloses an MRI system comprising a patient couch, a screen, a reflection plate and a frame. The patient couch is movable within a bore of the system along the center axis of the bore. The frame on the patient couch supports the reflection plate, such that a subject placed on the couch can see an image projected onto the screen via the reflection plate.

US 2017/123020 discloses a medical image diagnosis system including a gantry, a couch, a reflecting plate, and processing circuitry. The reflecting plate reflects an image output from an image output device. The processing circuitry, in a first case where the image is shown to an observer not through the reflecting plate, outputs a first image signal relating to a first image to the image output device. While in a second case where the image is shown to the observer through the reflecting plate, The processing circuitry outputs a second image signal relating to a second image to the image output device.

JP 2004-041411 discloses a method to present a visual stimulus in an MRI system. A dichroic mirror is used in an optical path insident on the eyeball of an examinee from substantially a front direction to present a visual stimulus from a projector and a screen. The eyeball is illuminated by an infrared lamp and movement of the eyeball is monitored by an infrared camera through the dichroic mirror, i.e. using a configuration in which the visual stimulus in the optical wavelength spectrum is reflected by the dichroic mirror while infrared light to illuminate and monitor the eye passes through.

SUMMARY OF THE INVENTION

An object of the invention is to provide a camera-based monitoring system for an magnetic resonance examination system that has a more effective range in the magnetic resonance examination system's examination zone.

This object is achieved according to the invention by a magnetic resonance examination system with an examination zone and comprising
a monitoring system with
a camera that is sensitive for infrared radiation and
at least one non-metallic mirror, in particular within the examination zone, arranging an optical pathway between a portion of the examination zone, via the non-metallic mirror, and the camera. The non-metallic mirror is a dielectric mirror having a macroscopically grated base.

The monitoring system of the invention functions to oversee the examination zone on the basis of images (whether by single image frames or by dynamic images) acquired by the camera. The camera has a (volumetric) range or field-of-view for which the camera is sensitive to obtain image information from. The non-metallic mirror(s) arranges for an optical path between a portion of the examination zone and the camera so that the camera can obtain image information from that portion. The non-metallic mirror(s) may be positioned in the examination zone e.g. by mounting to the inner wall of the examination zone. The non-metallic mirror(s) may also be disposed on auxiliary equipment in the examination zone, such as to a local radio frequency (RF) coil that is positioned on a patient carrier. It is e.g. practical to mount the non-metallic mirror on to an RF head coil. Further, the non-metallic mirror may be provided for on a separate frame outside of the examination zone. Notably, if no steps were taken, the portion at issue would be blocked from the camera's range. Such an obstacle is formed by an opaque object located in the camera's direct lines of sight into the examination zone. That object obstructs a portion of the examination zone form the field-of-view often camera. Such an obstacle may be auxiliary equipment that is placed in the examination zone, like local radiofrequency (RF) transmit or receive (T/R) antennas. Parts of a patient's body to be examined may also create an obstacle. The non-metallic mirror creates an optical pathway that circumvents one or more obstacles between the camera and the portion of the examination zone. More intricate circumventing optical pathways may be formed by providing a plurality of non-metallic mirrors onto the inner wall of the examination zone. The invention for example provides for more frontal views of the patient to be examined, even if obstacles are present in the examination zone. According to the invention fewer portions or none at all of the examination zone are taken out of the camera's range by objects potentially obstructing the directly lines of sight of the camera to the examination zone. The non-metallic mirror(s) are simple to mount onto the inner wall of the examination zone. The non-metallic mirrors are inexpensive to manufacture. The mounting of the non-metallic mirror(s) is easy to adapt to various imaging circumstances and the locations of the obstacles, such as local RF T/R antennae in the examination zone or to the size and position of the patient to be examined. The arrangement of a single camera and several non-metallic mirrors is relatively inexpensive e.g. as compared to employing several cameras, each of them overviewing a respective portion of the examination zone.

The non-metallic mirror(s) do not (electromagnetically) interfere with the radio frequency operation of the magnetic resonance examination system. That is, the sensitive RF acquisition of weak magnetic resonance signals is not affected by the non-metallic mirrors. Further, the non-metallic mirrors do not perturb the magnetic fields and the radiofrequency dynamic transmission field of the magnetic resonance examination system. The non-metallic mirrors are formed as dielectric mirrors. Such a dielectric mirror comprises a stack of layers of different refractive index. The layers may be glass layers having different refractive indices between adjacent layers forming a dielectric resonator. These stacked layers cause interference of light reflected from the interfaces of adjacent layers in the stack. In a simple implementation the dielectric mirror may be a glass plate, preferably dark coated at one side. This coated glass plate may be mounted with the non-coated side orientated towards the examination zone. This single layer glass plate has a reflectivity of about 4-5%, that allows the camera to acquire image information, albeit at low light intensity, from the examination zone.

These and other aspects of the invention will be further elaborated with reference to the embodiments defined in the dependent Claims.

The non-metallic mirror is a dielectric mirror having a macroscopically grated base. The non-metallic mirror may be formed by a stack of dielectric layers deposited on the macroscopically grated base. The macroscopically grated base may have patches that are each at an equal oblique angle to the normal of the lateral extension of the base. Such a macroscopically grated structure induces a tilted effective reflection from the layered stack of the non-metallic mirror. This tilt provides for an additional degree of freedom to configure the optical pathways to and from the non-metallic mirror. The mounting of the dielectric mirror may be arranged for easy mounting and removing so that a dielectric mirror with a suitable tilt can be employed for each examination, each with a particular configuration of the patient to be examined and auxiliary equipment. That is, a dielectric mirror may be selected with a tilt angle that provides for an optimum optical path from the examination zone to the camera with no or at most very few obstacles. To that end the mounting may be a simple mechanical slide mechanism with a clamp to attach/detach the dielectric mirror.

It is to be noted that the effective reflection, e.g. caused by the tilt of the patches of the grated base, may differ from a reflection with respect to the normal of the lateral extension of the base, such that the positioning (e.g. orientation) of the mirror is less constrained. For example, a good reflection along the optical path can be achieved while the mirror does not need to excessively protrude into the constrained volume of the scanner bore, e.g. may remain flush with, or at least to a lesser extent extended from, the wall of the examination area.

In another example of the magnetic resonance examination system of the invention, the non-metallic mirror may be mounted in an adjustable manner, e.g. by a hinge or pivot. This enables to vary the orientation of the non-metallic mirror relative to the inner wall, or relative to the principal axes of the examination zone. This provides for an additional degree of freedom to configure the optical pathways from the examination zone, via the non-metallic mirror to the camera. This widens the scope of circumventing obstacles in the examination zone and thus it is further avoided that portions of the examination zone are blocked from the camera's field-of-view.

Preferably, the monitoring system composing the camera and the non-metallic mirrors, and optionally one or more light sources, are operated in a narrow wavelength range and outside the visible wavelength range. A preferred example is to operate the system at a (infrared (IR)) wavelength, e.g. greater than 800 nm, e.g. a wavelength of about 850 nm+/− 20 nm. Then the multi-layer stacks can be configured to be reflective in that narrow wavelength range and have a high reflectivity for a wide range of angles of incidence or at least for a range of angles of incidence. This enables to configure the optical pathways to achieve a good coverage of the examination zone for the camera, in spite of obstacles that may be located in the examination zone. This also enables monitoring of the patient using IR light while the visible light level is low or dark which appears to be comfortable for many patients. For such a set-up a separate IR light source is installed for IR illumination of the examination zone.

In a further example, of the magnetic resonance examination system the light source is configured and positioned for directing its light beam via the non-metallic mirror into the examination zone. This configuration allows to illuminate several different areas on the patient with a common light source This light source may be located next to the camera to illuminate the examination zone using an optical pathway via a non-metallic mirror. In particular the optical pathway from the light source to the examination zone and from the examination zone to the camera may have one or more non-metallic mirrors in common. This enables to locate the light source as well as the camera outside the examination zone which simplifies the configuration of the magnetic resonance examination system and provides for more free bore width in the examination zone. In this way, e.g. in a cylindrical magnetic resonance examination system one end of the bore, i.e. the examination zone is left freely accessible for staff to position auxiliary equipment, connect auxiliary equipment e.g. by way of electrodes to the patient. The free end of the examination zone also reduces claustrophobic effects The wider the free bore space, the less discomfort for the (claustrophobic) patient, while wider bore sizes lead to a more expensive arrangement of main magnetic field coils and gradient magnetic field coils of the magnetic resonance examination system.

In another example of the invention, the non-metallic mirror is transparent in the visual wavelength range. In the framework of this example of the invention transparency means e.g. that the reflectivity is below 10% in the visual wavelength range of 400 nm to 800 nm. Such a non-metallic mirror being transparent in the visual spectrum appears non-distracting and hardly conspicuous to an observer, such as the operator and the patient to be examined. This visual transparency reduces distraction with the operator and the patient to be examined. This may particularly be advantageous to avoid a confusing or distressing view presented to the patient, and/or to provide a clear (unobstructed) view for an operator into the examination room, and/or to allow a further system component to provide visual stimuli or entertainment to the patient without obstruction by the observation system.

As another example, the monitoring system, in accordance with embodiments of the present invention, may function to obtain information from the patient, such as vital signs of the patient, and/or motion of the patient, and/or signs of distress of the patient (or, more general, patient mood detection), and/or photoplethysmography (PPG), and/or video-based detection of talking (or recognition of speech, e.g. of simple words or instructions based on facial features). Information on motion of the patient may include, for example, respiratory motion and/or cardiac motion, e.g. indicating the phase of respiratory and/or cardiac cycle phase. For example information on motion of the patient may be derived from image information of the outer hull of the patient's body. The information may be determined by processing (e.g. by an image-based motion detector) and/or by (direct) visual monitoring of the patient via the system by an operator or staff member. The respiratory and/or cardiac phase information may be applied to the reconstructor to correct the acquired magnetic resonance signals for motion or apply motion corrections to the reconstructed magnetic resonance images. For example, a cardiac trigger signal may be determined based on video signals from the camera. Cardiac triggering is particularly useful for cardiac MRI, for obvious reasons, but may also be applied more generally. For example, in neuro-imaging, artefacts in scans of the head and/or neck caused by pulsatile flow of blood and/or cerebrospinal fluid may be suppressed or reduced by such triggering technique or other compensation approach based on a cardiac phase signal. This may also be useful for quantitative measurement of blood flow in the carotid artery. Furthermore, a PPG signal can be extracted from the video signal by analyzing subtle intensity changes of skin pixels, e.g. in the face of a subject, such as at the forehead or at the cheeks.

The invention also pertains to a monitoring system to view the examination zone of an magnetic resonance examination system by way of a camera. The monitoring system of the invention comprises a camera and a non-metallic mirror, for placing in an examination zone so as to arrange an optical pathway between a portion of the examination zone, via the non-metallic mirror, and the camera. The non-metallic mirror is a dielectric mirror having a macroscopically grated base.

These and other aspects of the invention will be elucidated with reference to the embodiments described hereinafter and with reference to the accompanying drawing wherein

DETAILED DESCRIPTION OF THE EMBODIMENTS

Figure 1:
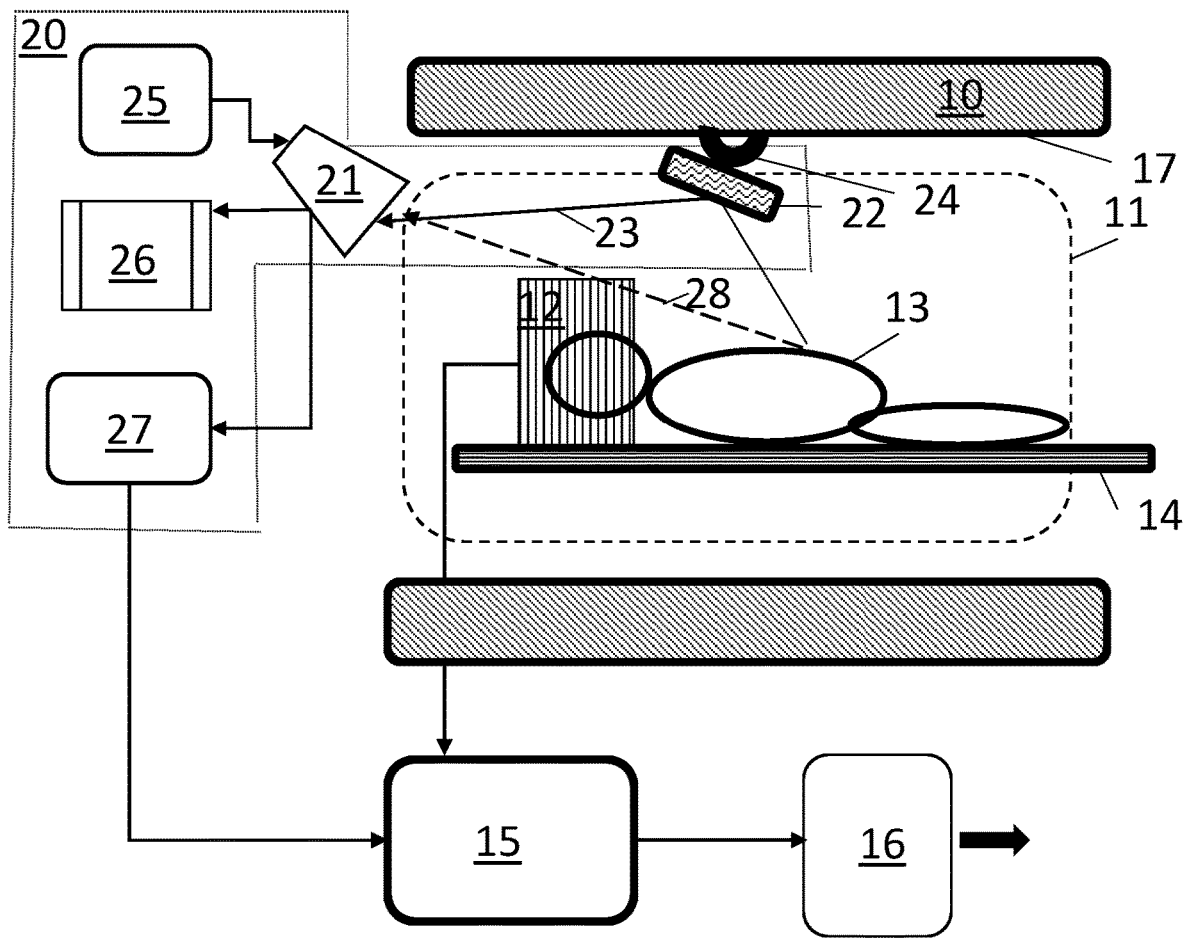
FIG. 1 shows a schematic side-elevation of an example of the magnetic resonance examination system incorporating the invention.

FIG. 1 shows a schematic side-elevation of an example of the magnetic resonance examination system incorporating the invention. The magnetic resonance examination system comprises a main magnet structure 10, which defines the examination zone. A patient to be examined 13 may be positioned on a patient carrier 14, e.g. a patient couch, into the examination zone. The main magnet structure includes a frame holding magnet windings to generate a stationary uniform magnetic field in the examination zone. The examination zone may be a cylindrical volume encompassed by a set of coaxial (super conductive) windings. The acquired magnetic resonance signals are applied to a reconstructor 15 which reconstructs magnetic resonance image(s) from the magnetic resonance signals. The reconstructed magnetic resonance images are finally output 16 for viewing, processing or storage. Auxiliary equipment, such as the RF T/R head coil 12 is placed in the examination zone, notably to acquire magnetic resonance signals from the patient's 13 head. For example, brain, cranial and/or cervical scans may be typically performed with the aid of such head coil, which may (at least to a large extent) fully enclose the head and neck of the patient, such that a direct view by the camera is mostly obscured.

The monitoring system 20 functions to obtain information from the patient to be examined, notably on vital signs and on motion. Notably, respiratory motion and cardiac motion may be derived from image information of outer hull of the patient's body. The camera 21 may be mounted close to one entry of the examination zone. For example, the camera may be integrated in, on mounted on, a flange of the MR bore (e.g. such that the usable free bore diameter is not affected or only minimally reduced, and/or to avoid or minimize interference with the operation of the MR system).

A camera control 25 is provided to control the camera 21, notably as to the direction into which the camera's range extends into the examination zone as to the focus length of the camera. Images of the inside of the examination zone 11 acquired by the camera 21 may be shown on a display 26. In this way, staff or an operator may visually monitor the patient to be examined in the examination zone. The image information acquired by the camera 21 may also be applied to a motion detector 27 (which may for example be implemented in software) to derive physiological information as respiratory and/or cardiac cycle phase of the patient to be examined from the image information acquired by the camera 21. The respiratory and/or cardiac phase information may be applied to the reconstructor 15 to correct the acquired magnetic resonance signals for motion and/or apply motion corrections to the reconstructed magnetic resonance images.

The monitoring system 20 further includes the non-metallic mirror 22 that may be mounted to the examination zone's inner wall 17 (e.g. the inner wall of the magnet bore enclosure). The monitoring system may comprise a pivot 24 to mount the non-metallic mirror such that its orientation can be controlled by the adjustable pivot. The non-metallic mirror 22 may be directly mounted to the inner wall 17 so that only little space in the examination zone is taken up by the non-metallic mirror. The non-metallic mirror generates (additional) optical paths 23 from a portion of the patient to be examined to the camera. Such an additional optical path 23 via the camera may circumvent obstructions, such as the RF T/R head coil 12 shown in FIGS. 1 and 2 as an example. Accordingly, the non-metallic mirror achieves that portions of the patient to be examined may be monitored, even if the camera's direct line of sight 28 is obstructed e.g. by the RF T/R head coil 12.

Alternatively, (or additionally) the non-metallic mirror may be mounted on, or formed as part of, a head T/R coil, e.g. as used for cervical, cranial and/or neuroradiological MR examinations. It is to be noted that integrating the mirror in or on the head coil may avoid costly or complex modification of existing equipment, e.g. of the scanner bore. While a relatively far distance between the camera, e.g. mounted on a flange of the bore, may result in a very limited field of view, e.g. only showing the forehead or part thereof, this may be sufficient for some applications, e.g. to monitor blood pulsation by slight variations in pixel intensity.

Figure 2:
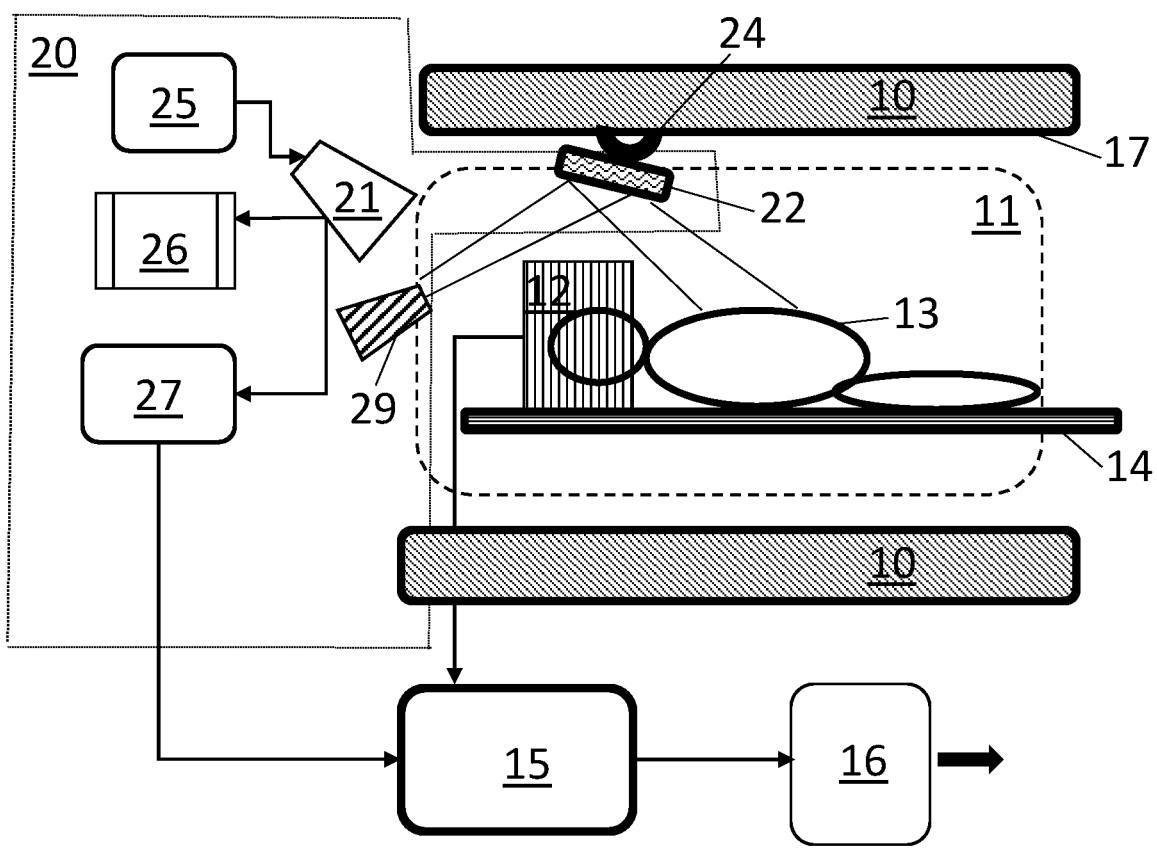
FIG. 2 shows a schematic side-elevation of another example of the magnetic resonance examination system incorporating the invention and FIG. 3 shows a detail of an example of the non-metallic mirror incorporated in the monitoring system.
Figure 3:
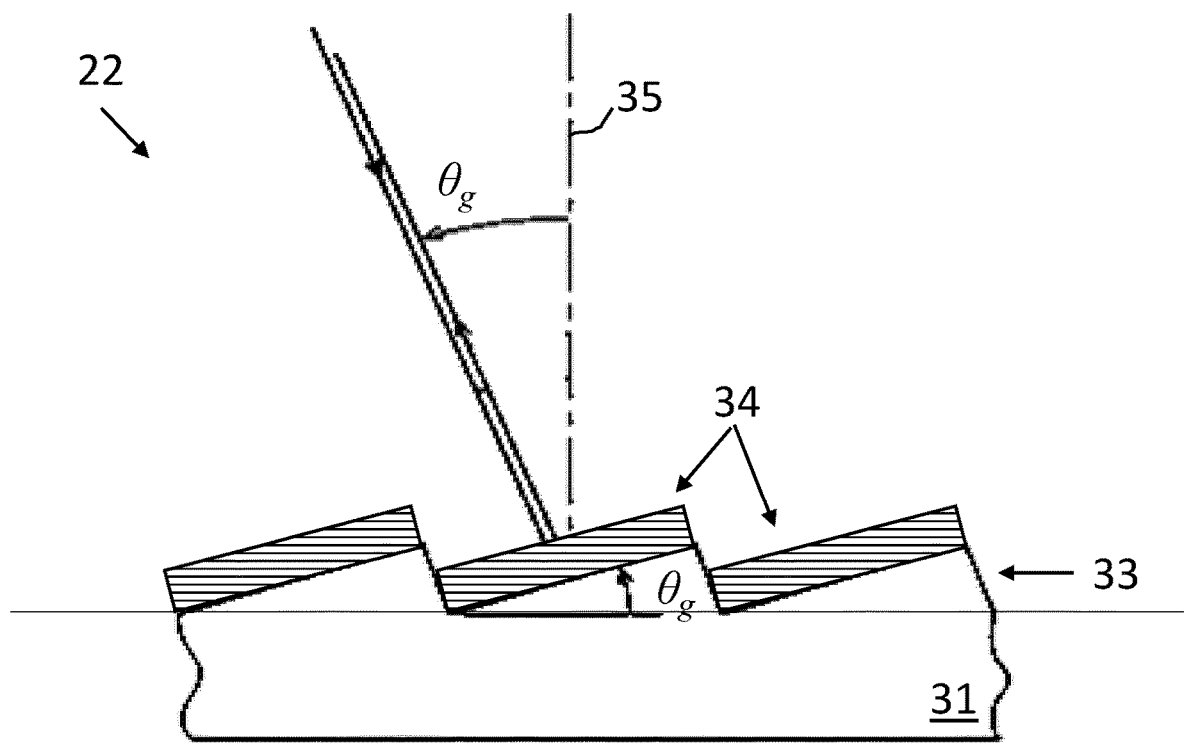

FIG. 2 shows a schematic side-elevation of another example of the magnetic resonance examination system incorporating the invention. The monitoring system of the magnetic resonance examination system shown in FIG. 2 is similar to that shown in FIG. 1. The monitoring system of FIG. 2 is additionally provided with an illumination system to illuminate (part of) the examination zone. The illumination system includes a light source 29, e.g. an infrared (IR) light source. For example, the light source may be located side-by-side with the camera 21. The light source may be located at a distance from the camera, but, for example, in generally the vicinity thereof. The light source(s) may thus illuminate a relevant part of the examination zone, for example directly and/or via the non-metallic mirror 22. In this way, parts of the examination zone that may be obstructed can be illuminated via the non-metallic mirror. Hence, the non-metallic mirror may achieve that the illumination of the examination zone is effective in spite of the presence of potentially blocking objects in the examination zone. FIG. 3 shows a detail of an example of the non-metallic mirror 22 incorporated in the monitoring system. The non-metallic mirror 22 comprises a base plate 31 with a macroscopically grated base 33 on one side of the base plate 31. The macroscopically grated base 31 has a plurality of patches 34 that are tilted relative to the normal 35 to the base plate's planar extension. That is the patches each are at an angle $\theta_g$ to the normal 35 to the base plate's planar extension. The lateral dimension of individual patches is substantially larger than the wavelength of the (IR) light from the examination zone. Thus, the patches induce an effective tilt to the angle of reflection for light form/to the examination zone. This effective tilt can be determined by the orientations of the individual patches.

The invention claimed is:

1. A magnetic resonance examination system with an examination zone, the system comprising:
   a monitoring system,
      wherein the monitoring system comprises;
         a camera, and
         a non-metallic dielectric mirror, and
         one of:
            an adjustable pivot provided on an inner wall of the magnetic resonance examination system, wherein the non-metallic dielectric mirror is mounted on the adjustable pivot, or
            a mechanical slide mechanism provided on the inner wall of the magnetic resonance examination system, wherein the mechanical slide mechanism is provided with a clamp to attach and/or detach the non-metallic dielectric mirror,
         wherein the non-metallic dielectric mirror is disposed within the examination zone,
         wherein the non-metallic dielectric mirror provides an optical pathway between a portion of the examination zone and the camera,
         wherein the non-metallic dielectric mirror comprises a base plate having a macroscopically grated base on one side of the base plate,
         wherein the macroscopically grated base comprises a plurality of patches,
         wherein at least some of the patches are tilted at corresponding angles relative to a normal to a planar extension of the base plate,
         wherein the corresponding angles determine a tilt to an angle of reflection for light from and/or to the examination zone.

2. The magnetic resonance examination system of claim 1, wherein said monitoring system is adapted to obtain information from a patient, based on an image output of the camera, wherein at least a portion of the patient is disposed in the examination zone, wherein said information includes at least one of:
   vital signs of the patient,
   movement of a body of the patient,
   an indication of a mood of the patient,
   a respiratory cycle phase for the patient, or
   a cardiac cycle phase for the patient.

3. The magnetic resonance examination system of claim 1, wherein the optical pathway circumvents auxiliary equipment that is disposed in the examination zone.

4. The magnetic resonance examination system of claim 1, wherein the non-metallic dielectric mirror comprises a stack of dielectric layers deposited on the macroscopically grated base.

5. The magnetic resonance examination system of claim 1, wherein said corresponding angles are equal oblique angles.

6. The magnetic resonance examination system of claim 1, wherein said non-metallic dielectric mirror is adjustably mounted so that its orientation to an inner wall of the magnetic resonance examination system can be varied.

7. The magnetic resonance examination system of claim 1, including a light source for directing a light beam via the non-metallic dielectric mirror into the examination zone.

8. The magnetic resonance examination system of claim 1, wherein the monitoring system further includes at least a second non-metallic mirror.

9. The magnetic resonance examination system of claim 1, wherein the camera is sensitive to infrared radiation and the non-metallic dielectric mirror is reflective of infrared radiation.

10. The magnetic resonance examination system of claim 1, wherein the non-metallic dielectric mirror is transparent in a visible wavelength range.

11. A monitoring system to view an examination zone of a magnetic resonance examination system, the monitoring system comprising:
   a camera,
   a non-metallic dielectric mirror,
      wherein the non-metallic mirror is configured to be placed in said examination zone so as to provide an optical pathway between a portion of the examination zone and the camera, and
   one of:
      an adjustable pivot provided on an inner wall of the magnetic resonance examination system, wherein the non-metallic dielectric mirror is mounted on the adjustable pivot, or
      a mechanical slide mechanism provided on the inner wall of the magnetic resonance examination system, wherein the mechanical slide mechanism is provided with a claim to attach and/or detach the non-metallic dielectric mirror,
   wherein the non-metallic dielectric mirror comprises a base plate having a macroscopically grated base on one side of the base plate,
   wherein the macroscopically grated base comprises a plurality of patches,
   wherein at least some of the patches are tilted at corresponding angles relative to a normal a planar extension of base plate,
   wherein the corresponding angles determine a tilt to an angle of reflection from light from and/or the examination zone.

12. The monitoring system of claim 11, wherein the non-metallic dielectric mirror comprises a stack of dielectric layers deposited on the macroscopically grated base.

13. The monitoring system of claim 11, wherein said corresponding angles are equal oblique angles.

14. The monitoring system of claim 11, wherein the camera is sensitive to infrared radiation and the non-metallic dielectric mirror is reflective of infrared radiation.

15. The monitoring system of claim 14, wherein the non-metallic dielectric mirror is transparent in a visible wavelength range.

16. The monitoring system of claim 11, further comprising a light source, wherein the light source is configured to illuminate at least the portion of the examination zone via the non-metallic dielectric mirror.

* * * * *